US00PP27597P2

(12) United States Plant Patent
Green, Jr.

(10) Patent No.: US PP27,597 P2
(45) Date of Patent: Jan. 24, 2017

(54) ***CAMELLIA* PLANT NAMED 'GREEN 01-006'**

(50) Latin Name: *Camellia sasanqua*
Varietal Denomination: Green 01-006

(71) Applicant: Robert M. Green, Jr., Fairhope, AL (US)

(72) Inventor: Robert M. Green, Jr., Fairhope, AL (US)

( * ) Notice: Subject to any disclaimer, the term of this patent is extended or adjusted under 35 U.S.C. 154(b) by 108 days.

(21) Appl. No.: 14/545,158

(22) Filed: Mar. 31, 2015

(51) Int. Cl.
*A01H 5/00* (2006.01)

(52) U.S. Cl.
USPC ..... Plt./244

(58) Field of Classification Search
USPC ..... Plt./226, 243, 244
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Camellia sasanqua* named 'Green 01-006', that is characterized by its dense, low, spreading plant habit suitable for use as a ground cover, its semi-double flowers with ruffled petal margins that are bright pink-purple in color, its floriferous bloom habit, and its good resistance to root rot (*Phytophora cinnamomi*) and dieback (*Glomerella cingulata*).

2 Drawing Sheets

Botanical classification: *Camellia sasanqua.*
Variety denomination: 'Green 01-006'.

BACKGROUND OF THE INVENTION

The present invention relates to a new and distinct cultivar of *Camellia* plant, botanically known as *Camellia sasanqua*, 'Green 01-006'. The new cultivar will be referred to hereafter by its cultivar name, 'Green 01-006'. 'Green 01-006' is a new perennial shrub grown for container and landscape use.

'Green 01-006' was derived from an ongoing breeding program conducted by the Inventor in Fairhope, Ala. The objectives of the breeding program are to develop new cultivars of *Camellia sasanqua* with compact plant habits, vigorous growth habits, improved disease resistance, and extended bloom periods. 'Green 01-006' originated as a seedling that arose from seed planted from open pollination of *Camellia sasanqua* cultivar 'Silver Dollar' (not patented) as the female parent in 2001 in Fairhope, Ala. The male parent is therefore unknown. The new *Camellia* was selected as a single unique plant in Fall of 2004.

Asexual propagaton of the new cultivar was first accomplished by stem cuttings by the Inventor in 2005 in Fairhope, Ala. Asexual propagation by stem cuttings has determined that the characteristics of this cultivar are stable and are reproduced true to type in successive generations.

SUMMARY OF THE INVENTION

The following traits have been repeatedly observed and represent the characteristics of the new *Camellia*. These attributes in combination distinguish 'Green 01-006' as a new and distinct cultivar of *Camellia*.

1. 'Green 01-006' exhibits a dense, low, spreading plant habit suitable for use as a tall ground cover.
2. 'Green 01-006' exhibits semi-double flowers with ruffled petal margins that are bright pink-purple in color.

3. 'Green 01-006' exhibits resistance to root rot (*Phytophora cinnamomi*) and dieback (*Glomerella cingulata*).

The female parent of 'Green 01-006', 'Silver Dollar', differs from 'Green 01-006' in having an taller less spreading plant habit, in having white flowers with a peony form. 'Green 01-006' can also be compared to the *Camellia sasanqua* cultivars 'Sarrel' (not patented) and 'Showa-No-Sakae' (not patented). Both culivars are similar to 'Green 01-006' in having a spreading plant habit. 'Sarrel' differs from 'Green 01-006' in having flowers with petals that are paler pink in color with ruffle-free margins, and in being less sun tolerant. 'Showa-No-Sakae' differs from 'Green 01-006' in having a less dense plant habit, in having leaves that are lighter green in color, in having heavy fruit production, in having less disease resistance, and in having a less uniform growth habit that eventually outgrows its use as a ground-cover.

BRIEF DESCRIPTION OF THE DRAWINGS

The accompanying colored photographs illustrate the overall appearance and distinct characteristics of the new *Camellia*. The photographs were taken of a 3 year-old plant of 'Green 01-006', as grown outdoors in a trial garden in Fairhope, Ala.

The photograph in FIG. 1 provides a view of the flower buds and flowers of 'Green 01-006'.

Figure 1:
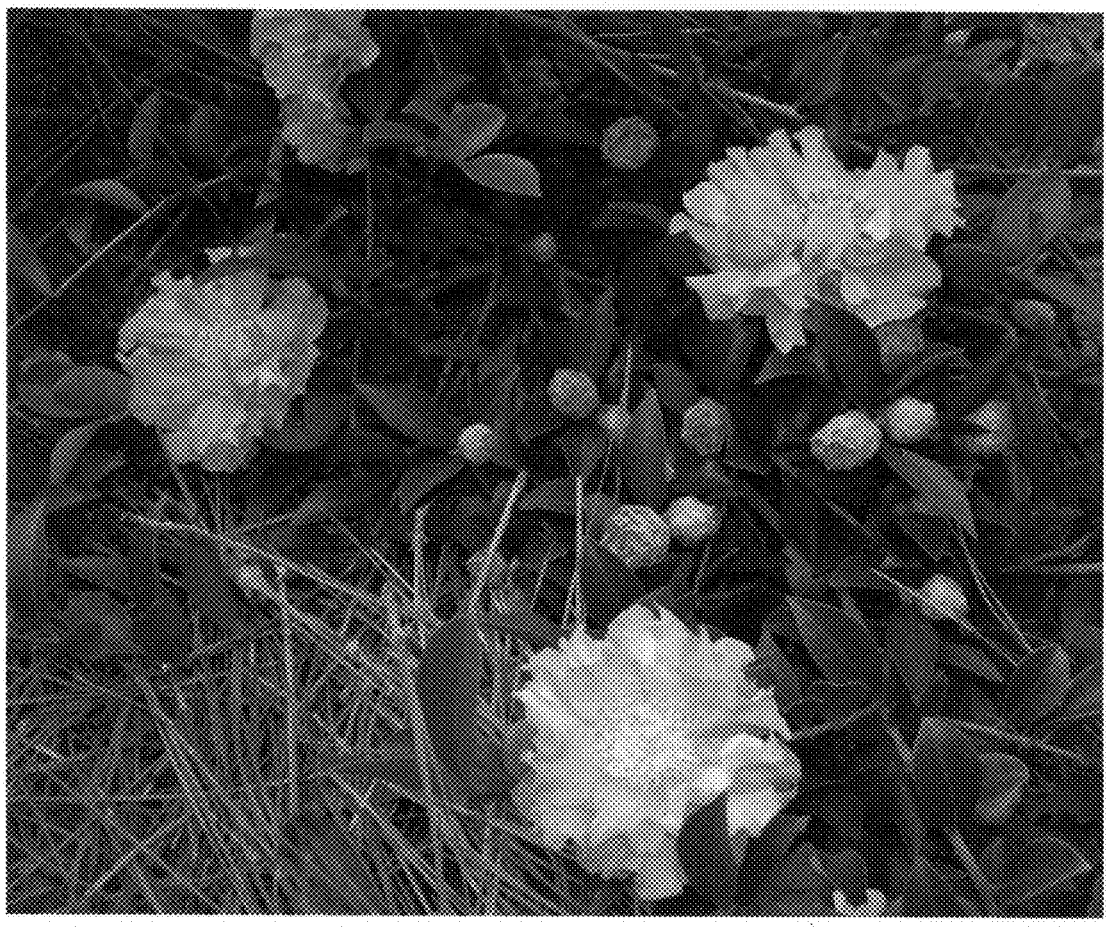
Figure 2:
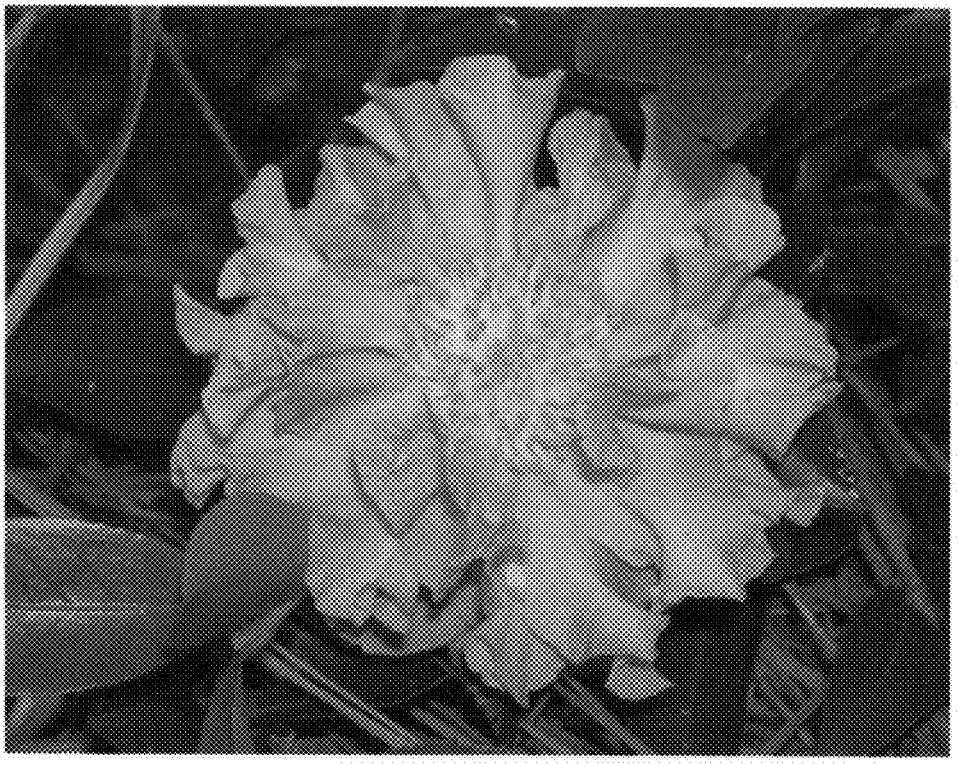

The photograph in FIG. 2 provides a close-up view of a flower of 'Green 01-006'.

Figure 3:
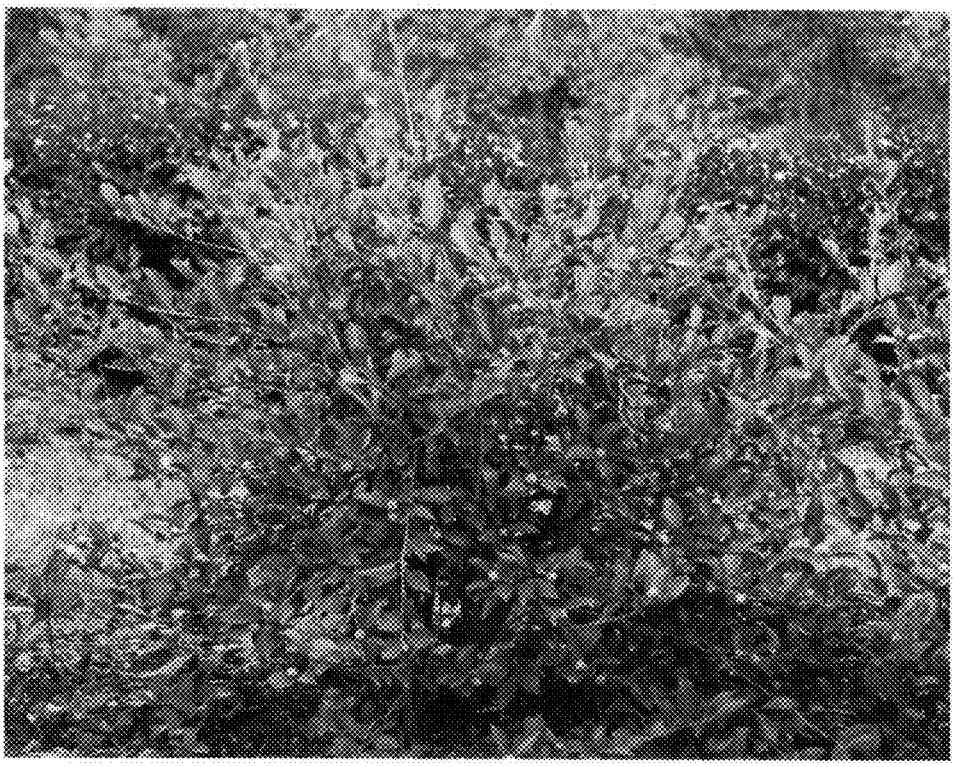

The photograph in FIG. 3 provides a side-view of the plant habit of 'Green 01-006'.

The colors in the photographs are as close as possible with digital photography techniques available, the color values cited in the detailed botanical description accurately describe the colors of the new *Camellia.*

DETAILED BOTANICAL DESCRIPTION

The following is a detailed description of 32 month-old plants of the new cultivar as grown ourtdoors in three-gallon containers in Fairhope, Ala. Plants were grown under 30% shade cloth with average day temperatures between 10 to 24° C. (50 to 75° F.) and average night temperatures between −1 to 10° C. (30 to 50° F.). The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—Seven to eight weeks beginning in mid to late fall in Fairhope, Ala.

*Plant type.*—Evergreen shrub.

*Plant habit.*—Dense, low, spreading, suitable for use as a tall ground cover.

*Height and spread.*—An average of 1.2 m in height and 2.1 m in spread when mature in the landscape, an average of 40 cm in height and 61 cm in spread as grown in a 3-gallon container.

*Hardiness.*—At least hardy in U.S.D.A. Zone 7b to 9.

*Diseases and pests.*—Has shown good resistance to root rot (*Phytophora cinnamomi*) and dieback (*Glomerella cingulata*).

*Propagation.*—Stem cuttings.

*Time required for root initiation.*—An average of 40 days.

*Time required for root development.*—About 6 months to fully develop in a 3 inch container.

*Growth rate.*—Moderately vigorous.

Branch description:

*Stem shape.*—Round.

*Stem strength.*—Strong.

*Stem color.*—Young; 165A with 166B towards the middle, mature bark; 200B suffused with 199A.

*Stem size.*—Main lateral branches; an average of 40 cm in length and 3 mm in width with secondary lateral branches a range of 8 to 20 cm in length and 3 to 5 mm in width.

*Stem surface.*—Young; bark-like, slightly glossy and sparsely covered with soft pubescent hairs; an average of 0.25 to 0.5 mm in length and 165A in color, mature; bark-like, slightly rough to touch.

*Branching.*—Densely branched with an average of 6 to 8 main lateral branches and 6 to 10 secondary laterals per main branch.

Foliage description:

*Leaf shape.*—Elliptic, oval, and obovate.

*Leaf division.*—Simple.

*Leaf base.*—Cuneate.

*Leaf apex.*—Bluntly acuminate to acute.

*Leaf fragrance.*—None.

*Leaf margins.*—Serrate.

*Leaf arrangement.*—Alternate.

*Leaf attachment.*—Petiolate.

*Leaf substance.*—Young leaves; thick and rubbery, mature leaves; thick.

*Leaf surface.*—Upper surface; smooth and glabrous and glossy, lower surface; smooth, glabrous, and satiny.

*Leaf size.*—An average of 5 cm in length and 2.5 cm in width.

*Leaf quantity.*—An average of 12 per branch 20 cm in length.

*Leaf venation.*—Pinnate, inconspicuous except for mid rib; upper surface 146C in color, lower surface 146B in color.

*Leaf color.*—Young and mature leaves upper surface; a blend of 139A and 147A, young and mature leaves lower surface; a blend of 137B and 146A.

*Petioles.*—Flattened in shape, an average of 2 mm in width and 5 mm in length, glabrous surface, N144A in color.

*Stipules.*—None.

Inflorescence description:

*Inflorescence type.*—Solitary.

*Flower number.*—4 to 5 per lateral stem.

*Flower fragrance.*—Slightly fragrant.

*Flower longevity.*—About one week, self cleaning.

*Flower type.*—Rotate, semi-double.

*Flower aspect.*—Outward to slightly upright, held at an average angle of 30 to 45° from stem.

*Flower size.*—An average of 6 cm in diameter and 2 cm in depth.

*Peduncles.*—None, flowers are sessile to stem.

*Flower buds.*—Globose in shape, an average of 2 cm in length and 1.5 cm in width, color; 144B in center, 144C on edges, 63A on apex.

*Sepals.*—An average of 6, ovate to rounded in shape and strongly cupped inward, imbricate, an average of 1 cm in length and width, rounded apex, truncate base, entire margin, color inner and outer surface; 144B with base 146B and edges 166A, outer surface covered with silky hairs, inner surface glabrous and satiny.

*Petals.*—An average of 25 to 33, oblong in shape, upper ruffled, an average of 4 cm in length and 3 cm width, color outer and lower surfaces when opening; a blend of 70C and 73B, color upper and lower surfaces when fully open; a blend of 70C and 73B, with center of the base 70D.

Reproductive organs:

*Pistil.*—Rudimentary, nonfunctional, somewhat obscured by stamens, 145B in color.

*Stamens.*—An average of 50, filaments; an average of 5 to 10 mm in length, 5D in color when young, darkening to 6B, anthers; an average of 2 to 3 mm in length and 155A in color, pollen; moderate in quantity 155A in color.

*Fruit and seed.*—Not present or very rarely produced and not available for data collecton.

It is claimed:

1. A new and distinct cultivar of *Camellia* plant named 'Green 01-006' as herein illustrated and described.

* * * * *